US012338212B2

(12) United States Patent
Kim et al.

(10) Patent No.: US 12,338,212 B2
(45) Date of Patent: Jun. 24, 2025

(54) ZEOLITE WITH IMPROVED HYDRO-ISOMERIZATION ACTIVITY

(71) Applicants: SK INNOVATION CO., LTD., Seoul (KR); SK ENMOVE CO., LTD., Seoul (KR)

(72) Inventors: Yeon Ho Kim, Daejeon (KR); Seung Woo Lee, Daejeon (KR); Yoon Kyung Lee, Daejeon (KR); Hee Jung Jeon, Daejeon (KR)

(73) Assignees: SK INNOVATION CO., LTD., Seoul (KR); SK ENMOVE CO., LTD., Seoul (KR)

( * ) Notice: Subject to any disclaimer, the term of this patent is extended or adjusted under 35 U.S.C. 154(b) by 179 days.

(21) Appl. No.: 18/366,571

(22) Filed: Aug. 7, 2023

(65) Prior Publication Data

US 2024/0059631 A1 Feb. 22, 2024

(30) Foreign Application Priority Data

Aug. 18, 2022 (KR) .................. 10-2022-0103117

(51) Int. Cl.
*B01J 29/70* (2006.01)
*B01J 35/50* (2024.01)
(Continued)

(52) U.S. Cl.
CPC ............. *C07C 5/222* (2013.01); *B01J 29/703* (2013.01); *B01J 35/50* (2024.01); *B01J 35/615* (2024.01);
(Continued)

(58) Field of Classification Search
CPC .... C07C 5/222; C07C 2529/65; B01J 29/703; B01J 29/7461; B01J 35/50; B01J 35/615;
(Continued)

(56) References Cited

U.S. PATENT DOCUMENTS

| 4,855,530 A | 8/1989 | LaPierre et al. |
| 4,962,269 A | 10/1990 | LaPierre et al. |

(Continued)

FOREIGN PATENT DOCUMENTS

| JP | 2003-531276 A | 10/2003 |
| JP | 6386562 B2 | 9/2018 |

(Continued)

OTHER PUBLICATIONS

Miao Zhang et al., Synthesis of ZSM-48 zeolites and their catalytic performance: a review, Catalysis Science & Technology, vol. 12, No. 16, Aug. 16, 2022, pp. 5097-5109, XP093106945, UK, ISSN: 2044-4753, DOI: 10.1039/D2CY00267A.

(Continued)

*Primary Examiner* — Bobby Ramdhanie
*Assistant Examiner* — Jason Y Chong
(74) *Attorney, Agent, or Firm* — IP & T GROUP LLP

(57) ABSTRACT

According to an aspect of the present invention, provided is a zeolite catalyst having an MRE structure for hydro-isomerization. The zeolite catalyst has an adsorption volume ratio of lutidine to collidine measured by Fourier-transform infrared spectroscopy (FTIR) using lutidine and collidine as adsorbents of greater than 3 and less than or equal to 10. According to an aspect of the present invention, provided is a method of hydro-isomerization for a hydrocarbon feedstock, including subjecting the hydrocarbon feedstock to a hydro-isomerization reaction under conditions of a temperature of 200° C. to 500° C., a hydrogen pressure of 1 to 200 atmospheres, a liquid space velocity (LHSV) of 1.0 to 10.0 $hr^{-1}$, and the hydrogen/feedstock ratio of 45 to 1780 $Nm^3/m^3$ in the presence of the zeolite catalyst.

10 Claims, 5 Drawing Sheets

(51) Int. Cl.
  *B01J 35/61* (2024.01)
  *B01J 35/63* (2024.01)
  *C07C 5/22* (2006.01)
  *C10G 45/64* (2006.01)

(52) U.S. Cl.
  CPC ......... *B01J 35/633* (2024.01); *C07C 2529/65* (2013.01)

(58) Field of Classification Search
  CPC ...... B01J 35/633; B01J 35/643; B01J 35/647; B01J 2229/18; C01B 39/48; C10G 45/54; C10G 45/64; C10G 65/08; C10M 101/02; C10M 101/025; C10M 109/02; C10M 177/00; C10M 2203/1006; C10N 2060/02; C10N 2070/00
  See application file for complete search history.

(56) References Cited

U.S. PATENT DOCUMENTS

| | | |
|---|---|---|
| 5,075,269 A | 12/1991 | Degnan et al. |
| 5,961,951 A | 10/1999 | Kennedy et al. |
| 9,687,828 B2 | 6/2017 | Lee et al. |

FOREIGN PATENT DOCUMENTS

| | | |
|---|---|---|
| KR | 10-2007-0001216 A | 1/2007 |
| KR | 10-1386733 B1 | 4/2014 |
| KR | 10-2068312 B1 | 1/2020 |
| KR | 10-2161426 B1 | 10/2020 |
| WO | 2007/070521 A1 | 6/2007 |
| WO | 2014/054439 A1 | 4/2014 |

OTHER PUBLICATIONS

C. Bouchy et al., Fischer-Tropsch Waxes Upgrading via Hydrocracking and Selective Hydroisomerization, Oil & Gas Science & Technology: Revue De L'institut Francais Du Petrole, Editions Technip Paris, FR, vol. 64, No. 1, Feb. 28, 2009, pp. 91-112, XP-002585754, ISSN: 1294-4475, DOI: 10.2516/OGST/2008047.

Emily Schulman et al., Two-Dimensional Zeolite Materials: Structural and Acidity Properties, Materials, vol. 13, No. 8, Apr. 12, 2020, p. 1822, XP055788461, DOI: 10.3390/ma13081822.

Extended European Search Report for the European Patent Application No. 23186887.8 issued by the European Patent Office on Dec. 21, 2023.

Lutidine(2,6-Lutidine)  Collidine(2,4,6-Trimethylpyridine)

ZEOLITE WITH IMPROVED HYDRO-ISOMERIZATION ACTIVITY

The present application claims priority to Korean Patent Application No. 10-2022-0103117, filed Aug. 18, 2022, the entire content of which is incorporated herein for all purposes by this reference.

BACKGROUND OF THE INVENTION

1. Field of the Invention

The present invention relates to a zeolite with improved hydro-isomerization activity and a hydro-isomerization reaction process of a feedstock using the same. More specifically, the present invention relates to a zeolite catalyst having an MRE structure in which acid sites exists near a pore mouth, and to a hydro-isomerization reaction process for C22+ hydrocarbons using the zeolite catalyst.

2. Description of the Related Art

The importance of hydro-isomerization reactions to convert n-paraffin to iso-paraffin is becoming increasingly important in refining processes such as lubricant manufacturing. This is due to the low low-temperature fluidity of long-chain n-paraffins, which does not meet the specifications of modern lubricant products. In particular, in recent years, the quality of raw materials has deteriorated due to rising oil prices, while the development of automobile engine technology has required higher quality products for lubricants. In this regard, the hydro-isomerization reaction for C15 or higher n-paraffins can be applied to a high-viscosity index high-grade lubricating oil manufacturing process.

The above-described hydro-isomerization reaction is known to be performed mainly by a bi-functional catalyst, which typically includes a metal component with a hydrogenation/dehydrogenation function and a support with acid sites for skeletal isomerization. In this regard, various materials such as silica-alumina, clay, zeolite, etc., are known as supports having acid sites. In particular, zeolite materials not only have a stable structure even under harsh reaction conditions, but also have a large specific surface area and a large number of acid sites, making them suitable for application in isomerization reactions.

In order to maximize the hydro-isomerization reaction and suppress the cracking of hydrocarbons to be treated as much as possible, studies have been conducted to use zeolite materials with excellent shape selectivity as zeolites, and among them, zeolite materials with a unidimensional 10-ring pore structure (ZSM-22, ZSM-23, EU-2, ZSM-48, etc.) have been reported to have excellent selectivity for the hydro-isomerization reaction.

According to the catalog of the International Zeolite Association (IZA), EU-2 belongs to the ZSM-48 family, along with ZSM-48, ZBM-30, and EU-11, and the ZSM-48 family has been given the three-letter skeletal structure code *MRE by the Structure Commission of the International Zeolite. They have similar XRD patterns, i.e., similar crystal structures.

Patent Registration No. 10-2161426 discloses a process of hydro-isomerization of hydrocarbon oils using a zeolite belonging to the ZSM-48 family as a catalyst and specific specifications of a zeolite catalyst used therein.

In addition, U.S. Pat. No. 5,961,951 discloses a series of processes for preparing a zeolite catalyst having a ZSM-48 structure by mixing silica, a trivalent metal oxide, an alkali metal oxide, ethylenediamine, and water, and specifications for zeolite catalysts prepared by the above processes.

However, while the patent document discloses a catalyst suitable for hydro-isomerization of n-paraffin having 10 or more carbon atoms, the patent references do not specifically address the specification of catalysts required for the hydro-isomerization of n-paraffins having more than 10 carbon atoms, for example, 22 or more carbon atoms.

SUMMARY OF THE INVENTION

An objective of the present invention is to provide a zeolite catalyst having an MRE structure for hydro-isomerization of a hydrocarbon feedstock having 22 or more carbon atoms, which is difficult to reach inside the zeolite catalyst due to the long carbon chain length.

According to an aspect of the present invention, there is provided a zeolite catalyst having an MRE structure for a hydro-isomerization reaction, in which the zeolite catalyst may have an adsorption amount ratio of lutidine to collidine of greater than 3 and less than or equal to 10 as measured by Fourier-transform infrared spectroscopy (FTIR) using lutidine and collidine as adsorbents.

According to an embodiment of the present invention, the zeolite catalyst having the MRE structure may be any one of EU2, ZSM-48 or ZBM-30 zeolite.

According to an embodiment of the present invention, with respect to the zeolite catalyst, an adsorption amount ratio of lutidine to collidine measured by FTIR using lutidine and collidine as adsorbents may be less than or equal to 8.

According to an embodiment of the present invention, the zeolite catalyst may have a silica-alumina ratio (SAR) of 100 to 250.

According to an embodiment of the present invention, the zeolite catalyst may have a SAR of 120 to 200.

According to an embodiment of the present invention, the zeolite catalyst may have a SAR of 150 to 170.

According to an embodiment of the present invention, the zeolite catalyst may have a total volume of pores having a diameter greater than 50 nm of less than 0.1 cc/g.

According to an embodiment of the present invention, the zeolite catalyst may have a total volume of pores having a diameter in a range of 2 to 50 nm of less than 0.2 cc/g.

According to an embodiment of the present invention, the zeolite catalyst may have a morphology selected from the group consisting of a granular shape, a needle shape, and a rod shape.

According to an embodiment of the present invention, the zeolite catalyst may have a Brunauer-Emmett-Teller (BET) surface area of greater than or equal to 250 $m^2/g$ and not greater than 300 $m^2/g$.

According to an aspect of the present invention, provided is a method of hydro-isomerization for a feedstock, including the step of subjecting the feedstock to a hydro-isomerization reaction under conditions of a temperature of 200° C. to 500° C., a hydrogen pressure of 1 to 200 atmospheres, a liquid space velocity (LHSV) of 1.0 to 10.0 lit', and a hydrogen/feedstock ratio of 45 to 1780 $Nm^3/m^3$ in the presence of a zeolite catalyst according to the foregoing aspects.

According to an embodiment of the present disclosure, the carbon number of at least some of the hydrocarbons in the feedstock may be at least 22.

According to the zeolite catalyst of the present invention, it is possible to increase the yield of hydro-isomerization while avoiding cracking of hydrocarbon feedstock for the preparation of lubricating base oils as much as possible. Furthermore, the hydro-isomerization reaction of feedstock using the zeolite catalyst of the present invention can proceed at a lower reaction temperature than when conventional zeolites are used.

These and other features and advantages of the present invention disclosure will become better understood from the following detailed description and figures.

DESCRIPTION OF THE EMBODIMENTS

Zeolite Catalysts for Hydro-Isomerization

According to an aspect of the present invention, there is provided a zeolite catalyst having an MRE structure for a hydro-isomerization reaction, in which the zeolite catalyst has an adsorption amount ratio of lutidine to collidine of greater than 3 and less than or equal to 10 as measured by FTIR using lutidine and collidine as adsorbents.

The adsorption ratio of lutidine to collidine may be greater than 3 to less than or equal to 10, greater than 3 to less than 9, greater than 3 to less than or equal to 8, greater than 3 to less than or equal to 7, greater than 3 to less than or equal to 6, greater than or equal to 3 to not greater than 5, greater than or equal to 3 to less than or equal to 4, greater than or equal to 4 to not greater than 10, greater than or equal to 4 to not greater than 9, greater than or equal to 4 to not greater than 8, greater than or equal to 4 to not greater than 7, greater than or equal to 4 to not greater than 6, greater than or equal to 4 to not greater than 5, greater than or equal to 5 to not greater than 10, greater than or equal to 5 to not greater than 9, greater than or equal to 5 to not greater than 8, greater than or equal to 5 to not greater than 7, greater than or equal to 5 to not greater than 6, greater than or equal to 6 to not greater than 10, greater than or equal to 6 to not greater than 9, greater than or equal to 6 to not greater than 8, greater than or equal to 6 to not greater than 7, greater than or equal to 7 to not greater than 10, greater than or equal to 7 to not greater than 9, or greater than or equal to 7 to not greater than 8.

Figure 1:
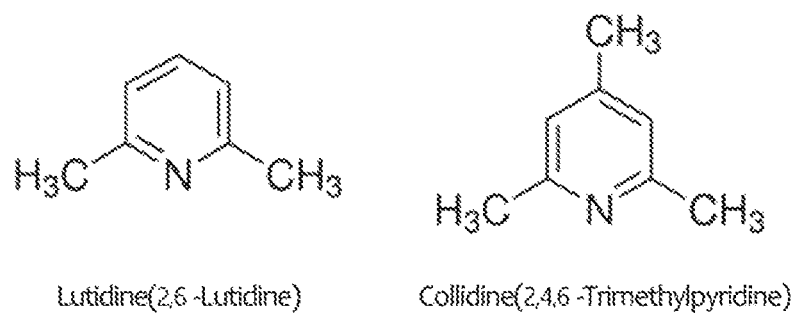
FIG. 1 is the chemical structure of lutidine and collidine, corresponding to the adsorbents used to determine the acid sites of the zeolite catalyst having the MRE structure of the present invention.

As shown in FIG. 1, lutidine has a pyridine chemical structure with two methyl groups, and has a smaller molecular size compared to collidine which has three methyl groups, allowing lutidine to enter deeper through the pores present in the MRE zeolite catalyst, but the absolute molecular size of lutidine and collidine makes it difficult for them to enter the deep interior of the catalyst through the pores of the MRE zeolite catalyst.

In other words, lutidine can enter the pore mouth of the MRE zeolite catalyst slightly inward from the pore entrance, while collidine can be present near the pore entrance, further outward than the pore mouth.

Figure 2:
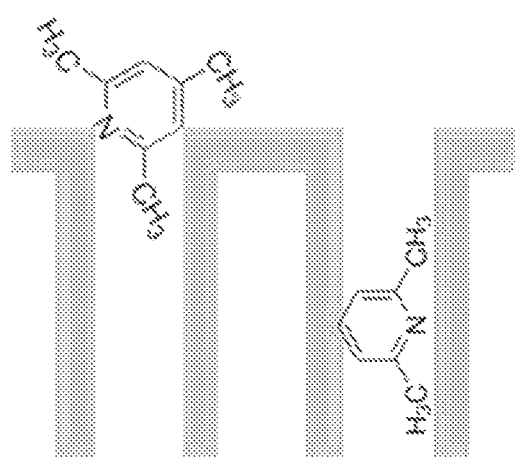
FIG. 2 is a schematic diagram showing the adsorbed positions of lutidine and collidine used as adsorbents to measure the acid sites of the zeolite catalyst having the MRE structure of the present invention.
Figure 3A:
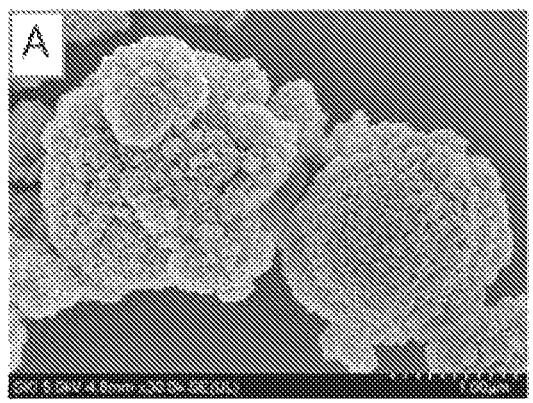
FIGS. 3a to 3d is a scanning electron microscope (SEM) image for observing the morphology of zeolite catalysts having MRE structures of Example samples A to D.
Figure 3B:
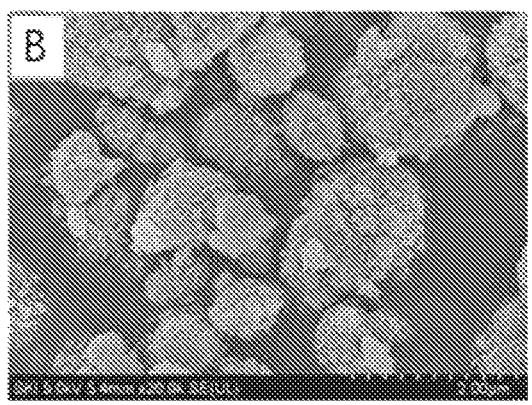
Figure 3C:
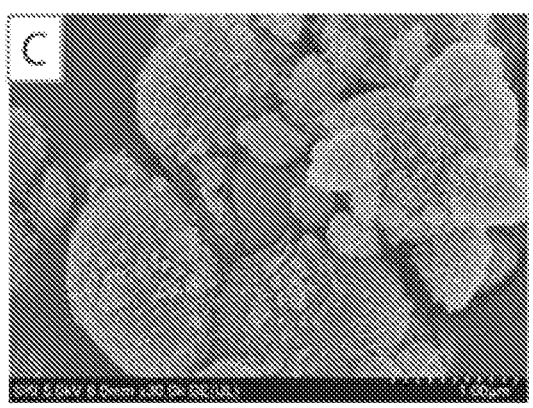
Figure 3D:
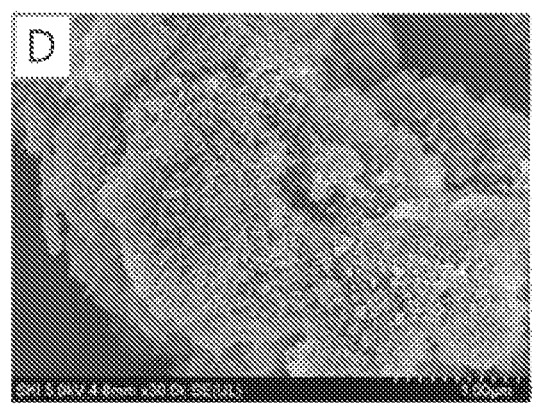

To observe the acid sites distribution of the MRE zeolite catalyst in the present invention, Fourier transform infrared spectroscopy (FTIR) with lutidine and collidine as adsorbents is used, and as mentioned above, lutidine can enter more in the interior of the pores compared to collidine, and FTIR peak measurements show that the ratio of the adsorbed amount of lutidine to collidine is greater than 3, which means that the acid sites of the MRE zeolite catalyst are mainly located near the pore mouth of the pores, not outside of the pores. As shown in FIG. 2, if the ratio of the adsorbed amount of lutidine to collidine is less than or equal to 3, the acid sites are mainly located on the outside of the pores, which may be disadvantageous from the point of view of reaction yield because the cracking reaction dominates over the hydro-isomerization reaction. On the other hand, if the ratio of the adsorbed amount of lutidine to collidine is greater than 10, the acid sites of the MRE zeolite catalyst are located inside the pore mouth, and when the metal is immersed in the MRE zeolite support, the dispersion of the metal may not be smooth, resulting in a decrease in the performance of the catalyst.

More specifically, the MRE zeolite catalyst may be imparted a dual functional catalytic function by immersing a metal, such as platinum, in the zeolite, in which the metal precursor is immersed in the zeolite in a solution dissolved in water, and the metal precursor has a size larger than the MRE zeolite pores, so the metal precursor cannot enter the pores and remains on the outer surface. The outer acid sites on the zeolite serve to evenly disperse the remaining metal on the outer surface of the zeolite, such as to prevent sintering during the reaction. If the adsorption capacity ratio of lutidine to collidine is greater than 10, the acid sites that help disperse the metal as described above will be located more internally, resulting in a lack of acid sites on the surface, and the metal may not disperse well.

In an embodiment, the zeolite catalyst may be any one of EU2, ZSM-48 or ZBM-30 zeolite. As described above, MRE is a three-letter skeletal structure code assigned to the ZSM-48 family by the International Zeolite Structure Committee, and a zeolite catalyst having the MRE structure is not limited to any zeolite belonging to the ZSM-48 family.

In an embodiment, the zeolite catalyst may have a SAR of 100 to 250. SAR means the molar ratio of $SiO_2$ to $Al_2O_3$ constituting the zeolite catalyst, and the zeolite catalyst having the MRE structure may have a SAR of 100 to 250, 100 to 200, 100 to 180, 120 to 250, 120 to 200, 120 to 180, 150 to 250, 150 to 200, 150 to 180, or 150 to 170. In the zeolite catalyst, some of the Si present in $SiO_2$ may be substituted with Al, and the charge of the substituted Al is 3+, which is different from Si having a charge of 4+, so the substitution causes an imbalance of charges, and H+ is introduced to maintain the neutrality of the charge in this state of imbalance, and this H+ acts as an acid sites. In other words, the more $Al_2O_3$ that makes up the zeolite catalyst, the more spots are present on the zeolite catalyst, and the smaller the SAR, the more favorable the catalyst is in terms of reaction yield. More specifically, if the SAR is greater than 250, there is less Al in the entire zeolite catalyst, so the number of acid sites where the conversion reaction occurs is also less, and in order to achieve the same level of reaction as a zeolite with more acid sites, the reaction temperature must be increased to allow more conversion reactions to occur at one acid site, which has the problem that the decomposition reaction may also be promoted at the same time as the reaction temperature is increased. In addition, when the SAR is less than 100, the EU-1 structure is mainly synthesized, not the EU-2 structure to be obtained in the present disclosure, and EU-1 is disadvantageous compared to the EU-2 structure in terms of isomerization yield.

In an embodiment, the zeolite catalyst may not include pores with a diameter greater than 50 nm.

According to the IUPAC pore size classification, pores with a width (diameter) of less than 2 nm are classified as micropores, pores with a width of 2 nm to 50 nm are classified as mesopores, and pores with a width of more than 50 nm are classified as macropores, and according to the above classification, the zeolite catalysts having the MRE structure of the present invention may not contain macropores.

The surface area and pore volume of the zeolite are determined using nitrogen gas adsorption/desorption equipment (e.g., Micromeritics' ASAP 2020). Prior to the test, the zeolite sample is degassed under vacuum at 350° C. for 3 hours. The degassed sample is adsorbed to nitrogen at 77K in a relative pressure ($p/p_0$) ranging from 10-6 to 0.997 and the amount of nitrogen gas adsorbed measured. The surface area was calculated based on BET theory and the pore volume was determined by t-plot method in accordance with the standard methodology of ISO 9277:2010 and ISO: 15901-2:2006.

More specifically, the volume of macropores in the zeolite catalyst may be less than 0.3 cc/g, less than 0.2 cc/g, and less than 0.1 cc/g. In an embodiment, the zeolite catalyst may not contain macropores.

In an embodiment, the zeolite catalyst may not include mesopores. For example, the zeolite catalyst may have a total volume of pores having a diameter in a range of 2 to 50 nm of less than 0.2 cc/g. In another embodiment, the zeolite catalyst may have a total volume of pores having a diameter of 2 nm to 50 nm and less than 0.1 cc/g. In yet another embodiment, the zeolite catalyst may not include pores having a diameter of 2 nm to 50 nm. When the volume of mesopores in a zeolite catalyst exceeds 0.2 cc/g, it becomes easier for C22+ hydrocarbons to enter the deeper interior of the catalyst, which is also the location of the hydrogenation isomerization reaction and the location of the cracking reaction, leading to the cleavage of n-paraffin chains through unwanted cracking as a side reaction.

In addition, there are two methods for preparing zeolite catalysts containing macropores and mesopores: first, preparing zeolite catalysts and subsequently etching the pores, and second, directly synthesizing zeolites containing macropores and mesopores using surfactants. In the former case, there is zeolite that is lost by the etching process, which increases the manufacturing cost per unit weight, and in the latter case, special surfactants must be used, and the raw material cost of these surfactants is high, and the process cost of filtering the zeolite and treating the foam of the remaining mother liquor in the zeolite recovery step after synthesis is high, which also results in a high manufacturing cost. As described above, the zeolite catalyst of the present disclosure may not include macropores and mesopores, and thus has an advantage in terms of manufacturing cost.

As described above, the zeolite catalyst according to the present disclosure may not include macropores and mesopores, and may include only pores (micropores) having a diameter of less than 2 nm. Pores with a diameter of less than 2 nm are not easy for C22+ n-paraffin to enter the zeolite catalyst through the pores, preventing C22+ n-paraffin from cracking at acid sites inside the zeolite. In addition, as described above, the acid sites of the zeolite catalyst are located in the pore mouth, so that C22+ n-paraffin can be isomerized into iso-paraffin through a desired hydro-isomerization reaction without approaching the inside of the catalyst.

In an embodiment, the zeolite catalyst may have a morphology selected from the group consisting of a granular shape, a needle shape, and a rod shape. The morphology is observed by SEM images as shown in FIGS. 3a to 3d. From the viewpoint of improving the hydro-isomerization reaction yield of hydrocarbon feedstock and reducing weighted average bed temperature (WABT), the zeolite catalyst may have a granular shape morphology.

In an embodiment, the zeolite catalyst may have a BET surface area of greater than 250 m$^2$/g and less than 300 m$^2$/g. The specific surface area of zeolite catalysts is measured using BET equipment (e.g., Micromeritics' ASAP 2020), which is based on BET theory and measures the amount of gas adsorbed on a solid surface as the pressure change in a vacuum chamber while varying the pressure of the gas at a constant temperature. For example, after pretreatment in a vacuum state at 350° C. for 3 hours, N$_2$ is adsorbed, and the amount of N$_2$ gas adsorbed can be measured and calculated from the BET adsorption isotherm.

More specifically, the zeolite catalyst may have a specific surface area of greater than or equal to 250 m$^2$/g and not greater than 300 m$^2$/g, greater than or equal to 250 m$^2$/g and not greater than 290 m$^2$/g, greater than or equal to 250 m$^2$/g and not greater than 280 m$^2$/g, greater than or equal to 250 m$^2$/g and not greater than 270 m$^2$/g, greater than or equal to 250 m$^2$/g and not greater than 260 m$^2$/g, greater than or equal to 260 m$^2$/g and not greater than 300 m$^2$/g, greater than or equal to 260 m$^2$/g and not greater than 290 m$^2$/g, greater than or equal to 260 m$^2$/g and not greater than 280 m$^2$/g, greater than or equal to 260 m$^2$/g and not greater than 270 m$^2$/g, greater than or equal to 270 m$^2$/g and not greater than 300 m$^2$/g, greater than or equal to 270 m$^2$/g and not greater than 290 m$^2$/g, greater than or equal to 270 m$^2$/g and not greater than 280 m$^2$/g, greater than or equal to 280 m$^2$/g and not greater than 300 m$^2$/g, greater than or equal to 280 m$^2$/g and not greater than 290 m$^2$/g, and greater than or equal to 290 m$^2$/g and not greater than 300 m$^2$/g.

As described above, the zeolite catalyst of the present disclosure may not include macropores and mesopores but includes micropores, resulting in a high BET surface area, which is an increase from the BET surface area of about 220 m$^2$/g for a typical MRE-structured zeolite. All other conditions being equal, a low BET surface area means that the zeolite structure has not grown properly, which typically indicates low catalytic activity.

Hydro-Isomerization Process Using Zeolite Catalyst

According to an aspect of the present invention, there is provided a process for converting n-paraffin-containing feedstock (including mineral, synthetic, and/or biomass-derived feedstock) to iso-paraffin by an isomerization reaction while supplying hydrogen in the presence of the aforementioned zeolite catalyst. Such feedstock may typically contain at least about 15% by weight of n-paraffin, and more particularly at least about 40% by weight Specific examples of the above feedstock include hydrocarbon oils having a boiling point (as measured by ASTM D-86 or ASTM D-2887) in the range of at least about 150° C. to 580° C., specifically hydrocarbon oils in the range of lubricating base oils.

In particular, the pores of the aforementioned zeolite catalysts are micropores having a diameter of less than 2 nm, and are therefore effectively applicable to hydrocarbon oils having a carbon number of about 22 or more and having a lubricating base oil boiling point in the range of about 360° C. to 580° C. More specifically, the zeolite catalyst having the above micropores is effective in the hydro-isomerization of hydrocarbon oils having a carbon number of 22 to 35, 22 to 30, 22 to 25, 25 to 35, 25 to 30, 27 to 35, or 27 to 30.

In an embodiment, the hydrocarbon feedstock may contain n-paraffins (wax component) at least about 15% by weight, specifically at least about 40% by weight. In addition, the feedstock may contain, for example, about 10 ppm (wt) or less (specifically, about 5 ppm (wt) or less) of nitrogen and/or about 10 ppm (wt) or less (specifically, about 5 ppm (wt) or less) of sulfur.

The hydro-isomerization process is performed on the hydrocarbon feedstock, for example, at a temperature of about 200° C. to 500° C., in particular about 220° C. to 450° C., and more in particular about 240° C. to 400° C.), a hydrogen pressure of about 1 to 200 atmospheres, in particular about 100 to 180 atmospheres, and more in particular about 130 to 150 atmospheres, a space velocity (LHSV) of about 0.1 to 10 $hr^{-1}$, in particular about 0.5 to 5 $hr^{-1}$, and more in particular about 1 to 2 $hr^{-1}$), and a hydrogen/feedstock ratio of about 45 to 1780 $Nm^3/m^3$, in particular about 200 to 1000 $Nm^3/m^3$, and more in particular about 480 to 530 $Nm^3/m^3$.

After undergoing the aforementioned hydro-isomerization process, the pour point of the hydrocarbon oil as the feedstock may be reduced, for example, by at least about −12° C., and more specifically by at least about −18° C. Further, when the feedstock is a hydrocarbon oil in the range of lubricating base oil boiling point, the viscosity index may be in the range of, for example, at least about 60, about 70 to 160, about 80 to 150, and about 120 to 140. Hereinafter, examples are presented to help the understanding of the present disclosure. It is noted that the following examples are provided for improved understanding of the present disclosure, and the present disclosure may not be limited to the examples only.

Preparation Example

A zeolite catalyst according to an embodiment of the present disclosure was prepared through the following process, and reagents used in the processes of Preparation Examples and Comparative Preparation Examples are shown in Table 1 below.

TABLE 1

| Reagent | Manufacturer |
|---|---|
| Aluminum hydroxide | Sigma-Aldrich |
| LUDOX ® HS-40 colloidal silica | Sigma-Aldrich |
| Cetyltrimethylammonium chloride solution (25 wt % in H2O) | Sigma-Aldrich |
| Sodium hydroxide, bead, >98.0% | SUMCHUN CHEMICALS |
| Sodium Hydroxide Solution (20 wt % in H2O) | SUMCHUN CHEMICALS |
| CATAPAL A | Sasol |
| Hexamethonium Chloride Dihydrate (>99.0%) | TCI |

Preparation of Sample A

Solution A1 was prepared by completely dissolving 44.73 g of sodium hydroxide, bead, >98.0% in 1121.49 g of deionized water, solution A2 was prepared by adding 5.06 g of aluminum hydroxide to solution A1 and completely dissolving the added aluminum hydroxide, and solution A3 was prepared by adding 37.49 g of hexamethonium chloride dihydrate (>99.0%) to solution A2, and completely dissolving the added hexamethonium chloride dihydrate. Thereafter, while stirring the solution A3 at room temperature at 250 rpm, 780.30 g of LUDOX® HS-40 colloidal silica was added dropwise for about 1 hour to form a gel. The prepared gel was poured into a 2 L hastelloy autoclave, and aged at room temperature under atmospheric pressure for 24 hours with agitation at 600 rpm. The aged gel was heated to 165° C. for 85 minutes at constant rate, and hydrothermally synthesized at 165° C. for 48 hours under autogenous pressure with agitation at 600 rpm.

Thereafter, the as-synthesized product was thoroughly washed with deionized water until the pH was neutral, and then dried in an oven at 50° C. overnight. The as-synthesized zeolite as heated for removal of organic matter in a muffle furnace from room temperature to 450° C. and remained at 450° C. for 1 hour and then heated from 450° C. to 550° C. and remained at 550° C. for 6 hours. The washed and calcined zeolite is referral to as Na-EU2.

The Na-EU2 was ion-exchanged twice at room temperature with 1 M $NH_4NO_3$ solution to exchange Na ions contained therein with $NH^{4+}$ ions. The ion exchanged zeolite is referred to as NH4-EU2.

Figure 5:
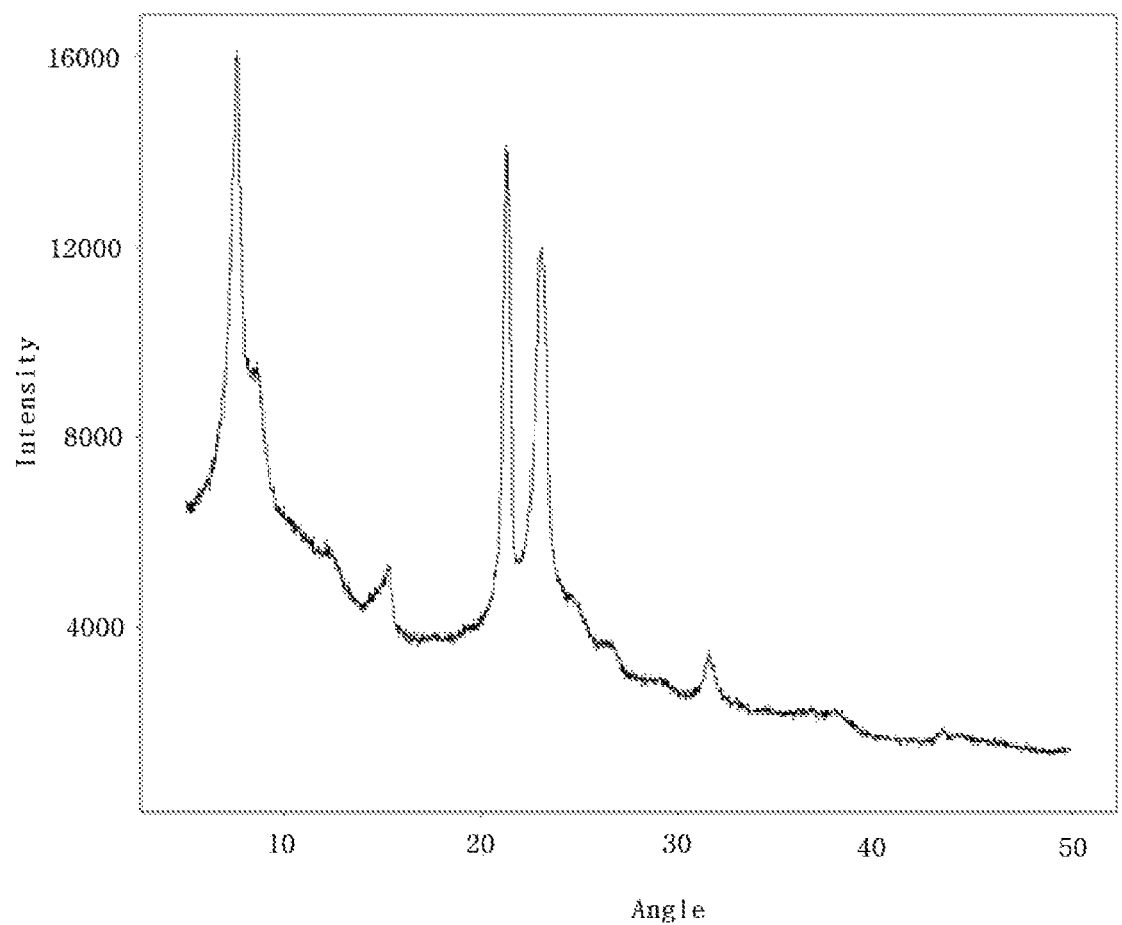
FIG. 5 shows XRD data for MRE structure of Example sample A.

Then, 42 g of NH4-EU2 was mixed with 18 g of PURAL pseudoboehmite by roll mixer for 12 hours at 70 rpm, which was impregnated with 1% $Pt(NH_3)_4(NO_3)_2$ solution 36 g and 60% nitric acid 1.32 g solution by incipient wetness impregnation. The catalyst was sufficiently dried at room temperature and then calcined in a muffle furnace at 120° C. for 3 hours and 500° C. for 3 hours to obtain a final zeolite catalyst sample A. FIG. 5 shows XRD data for the final zeolite catalyst sample A Comparative Preparation Example Samples B to D were prepared through the following process using the same reagents as in the above Preparation Example.

Sample B

After gel formation, zeolite catalyst sample B was prepared by the same process as sample A, except that the agitation speed was 400 rpm in the hydrothermal step without aging step.

Sample C

Solution C1 was prepared by adding 4.59 g of CATAPAL A to 223.65 g of 20% by weight of NaOH solution and completely dissolving the added CATAPAL A, solution C2 was prepared by pouring 942.57 g of deionized water into solution C1 and completely dissolving, and then solution C3 was prepared by adding 37.49 g of hexamethonium chloride dihydrate (>99.0%) and completely dissolving the added hexamethonium chloride dihydrate. Thereafter, while stirring solution C3 at room temperature at 250 rpm, 780.30 g of LUDOX® HS-40 colloidal silica was added dropwise for about 1 hour to form a gel. Thereafter, the prepared gel was poured into a 2 L hastelloy autoclave, heated from room temperature to 165° C. for 5 hours at constant rate with agitation speed at 600 rpm, and then hydrothermally synthesized at 165° C. under autogenous pressure for 48 hours.

Thereafter, zeolite catalyst sample C was prepared through the same steps of washing, drying, calcining, and ion exchange as in the preparation process of sample A.

Sample D

Solution D1 was prepared by completely dissolving 204.56 g of 20% by weight NaOH solution in 811.15 g of deionized water, solution D2 was prepared by adding 5.17 g of aluminum hydroxide to solution D1 and completely dissolving the added aluminum hydroxide, and solution D3 was prepared by adding 20.55 g of hexamethonium chloride dihydrate (>99.0%) and completely dissolving the added hexamethonium chloride dihydrate. Thereafter, solution D4 was prepared by adding 60.40 g of cetyltrimethylammonium chloride solution (25% by weight in $H_2O$) to solution D3 and completely dissolving the added cetyltrimethylammonium chloride solution. While stirring the prepared solution D4 at 250 rpm at room temperature, 798.13 g of LUDOX® HS-40 colloidal silica was added dropwise for about 1 hour to form a gel, and the prepared gel was poured into a 2 L hastelloy autoclave, heated from room temperature to 165° C. for 5 hours at constant rate with agitation speed at 600 rpm, and then hydrothermally synthesized at 165° C. under autogenous pressure for 48 hours.

Thereafter, zeolite catalyst sample D was prepared through the same steps of washing, drying, calcining, and ion exchange as in the preparation process of sample A.

Example

1. Measurement of Acid Sites Distribution of Zeolites

In order to measure the acid sites distribution of samples A to D, an FTIR measurement method was used. Measurements were performed as follows:
1) Manufacture of 15 mg self-supporting zeolite wafer with 1.3 cm diameter.
2) Loading zeolite wafers into high-temperature/high-pressure cells.
3) At a pressure of $1.0 \times 10^{-8}$ torr, the temperature was raised to 550° C. at a rate of 10° C./min, followed by evacuation for 2 hours.
4) At a pressure of $1.0 \times 10^{-8}$ torr, cooling to 150° C.
5) Repeated injection of lutidine or collidine until the adsorption peak area no longer increases under vacuum and at a temperature of 150° C.
6) Remove physically adsorbed lutidine or collidine for 2 hours at a pressure of $1.0 \times 10^{-8}$ torr and a temperature of 200° C.
7) At a pressure of $1.0 \times 10^{-8}$ torr, measure the adsorption area after reducing the temperature to 150° C.

Figure 4:
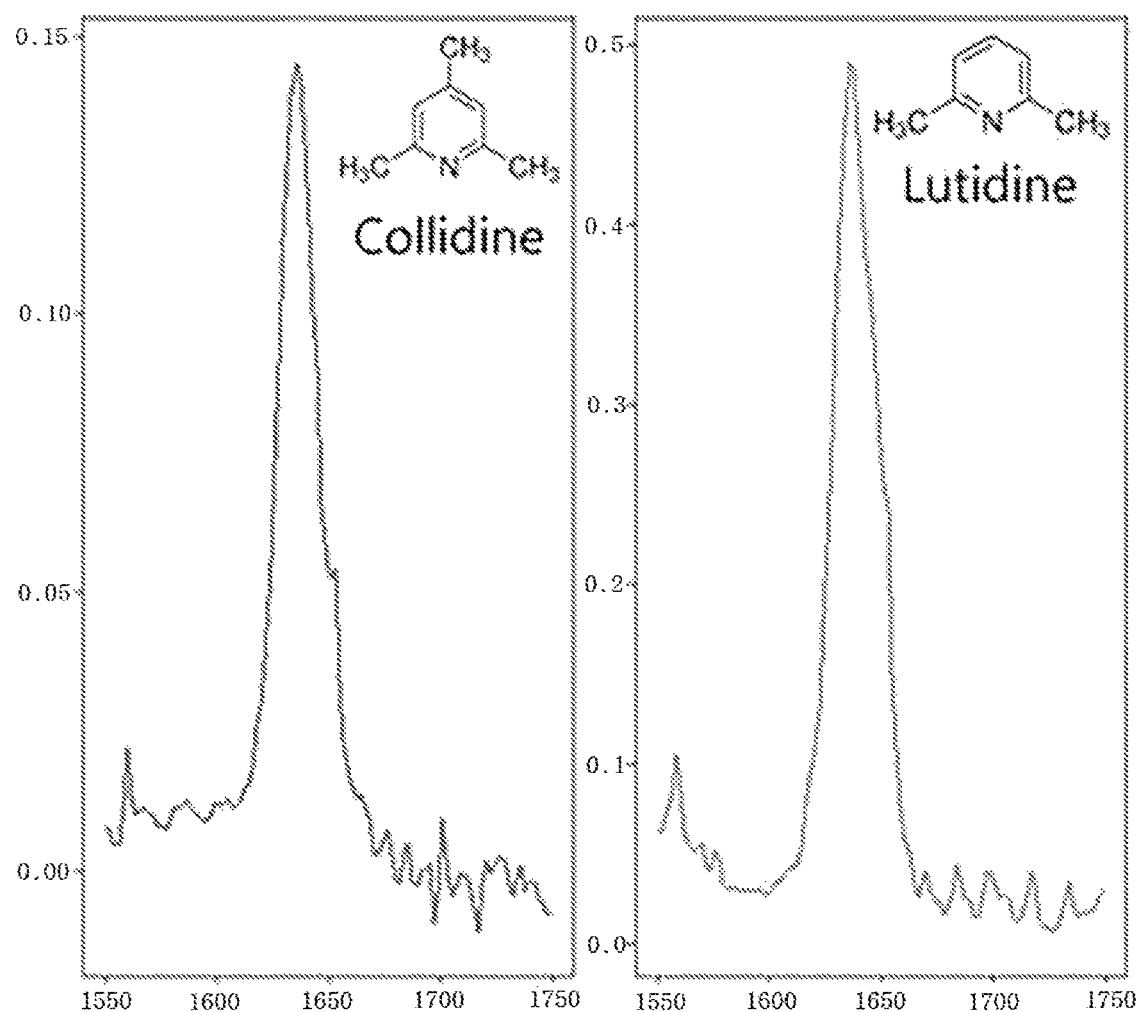
FIG. 4 shows BUR peak data for lutidine and collidine according to an Example of the present disclosure.

The FTIR peaks of collidine and lutidine according to the above FTIR measuring method are shown in FIG. 4, and the FTIR adsorption areas for lutidine and collidine respectively were obtained by integrating over the wavenumber range of 1600 $cm^{-1}$ to 1700 $cm^{-1}$. Specific peak areas for each sample are as listed in Table 3 below.

2. Hydro-Isomerization Reaction Yield and Reaction Temperature Measurement of Zeolite A feedstock having the properties in Table 2 below was introduced into a hydro-isomerization reaction in the presence of a zeolite catalyst of any of the above samples A to D at a hydrogen pressure of about 160 atmospheres, a liquid space velocity (LHSV) of about 1.7 $hr^{-1}$, a hydrogen/feedstock ratio of about 500 $Nm^3/m^3$, and a reaction temperature of (pour point target–18° C.).

TABLE 2

|  | Feedstock |
| --- | --- |
| Specific gravity | 0.8361 |
| 10% | 439.2 |
| 50% | 473.6 |
| 90% | 524.8 |
| Content of sulfur | 2.2 |
| Content of nitrogen | <1.0 |
| Kinematic viscosity index | 6.551 |
| Pour point(° C.) | 48 |

The SAR, BET surface area, volume fraction of mesopores, peak area of lutidine and collidine, lutidine/collidine peak area ratio, weighted average bed temperature (WABT), and the hydro-isomerization reaction yield of samples A to D according to the above embodiments are shown in Table 3 below.

TABLE 3

| Sample | A | B | C | D |
| --- | --- | --- | --- | --- |
| SAR | 152.5 | 118 | 127 | 164.8 |
| BET | 261.8 | 216.8 | 253.1 | 318.5 |
| $V_{meso}$ | 0.10 | 0.11 | 0.12 | 0.19 |
| Lutidine | 11.09 | 3.28 | 4.99 | 10.71 |
| Collidine | 2.77 | 1.41 | 1.97 | 2.54 |
| Lu/Col | 4.00 | 2.33 | 2.53 | 4.22 |
| WABT | 316 | 334 | 316 | 326 |
| Yield | 92.5 | 91.8 | 85.6 | 89.4 |

As can be seen in Table 3, the highest yield of 92.5% was obtained when the hydro-isomerization reaction was performed using the zeolite catalyst of sample A, which satisfied a SAR of more than 150, a BET surface area of more than 250, and a lutidine/collidine peak area ratio of more than 3 but less than 10, confirming that such a high yield can be achieved at a low reaction temperature (i.e., WABT).

In addition, referring to FIGS. 3a to 3d in relation to the morphologies of samples A to D, it can be seen that sample A represents a granular type (FIG. 3a), sample B represents an amorphous type in which the growth of the crystal is not completely finished (FIG. 3b), sample C represents a needle type (FIG. 3c), and sample D represents a rod type (FIG. 3d), and due to these morphologies, sample B of the amorphous type in Table 3 exhibits a significantly lower BET surface area compared to samples A, C, and D having other types of morphologies.

While the present invention has been described by referring to specific examples, it should be understood that many variations of the described examples may be envisioned by the skilled person after having read the present invention disclosure without departing from the scope of the invention as defined in the appended claims.

What is claimed is:

1. A zeolite catalyst having an MRE structure for a hydro-isomerization reaction,
   wherein the zeolite catalyst having an MRE structure is selected from the group consisting of EU-2, ZSM-48, and ZBM-30,
   wherein the zeolite catalyst has an adsorption volume ratio of lutidine to collidine greater than 3 and less than or equal to 10, as measured by Fourier-transform infrared spectroscopy (FTIR) using lutidine and collidine as adsorbents,
   wherein the zeolite catalyst has a silica-alumina ratio (SAR) of 100 to 200, and
   wherein the zeolite catalyst has a BET surface area greater than or equal to 250 $m^2/g$ and not greater than 300 $m^2/g$.

2. The zeolite catalyst of claim 1, wherein an adsorption volume ratio of lutidine to collidine is greater than or equal to 8 measured by FTIR using lutidine and collidine as adsorbents.

3. The zeolite catalyst of claim 1, wherein the zeolite catalyst has silica-alumina ratio (SAR) of 120 to 200.

4. The zeolite catalyst of claim 1, wherein the zeolite catalyst has silica-alumina ratio (SAR) of 150 to 170.

5. The zeolite catalyst of claim 1, wherein the zeolite catalyst has a total volume of pores having a diameter in a range of greater than 50 nm of less than 0.1 cc/g.

6. The zeolite catalyst of claim 5, wherein the zeolite catalyst has a total volume of pores having a diameter in a range of 2 to 50 nm of less than 0.2 cc/g.

7. The zeolite catalyst of claim 1, wherein the zeolite catalyst has a morphology selected from the group consisting of a granular shape, a needle shape, and a rod shape.

8. The zeolite catalyst of claim 7, wherein the zeolite catalyst has a granular shape.

9. A method of hydro-isomerization for a hydrocarbon feedstock, the method comprising:
   subjecting the hydrocarbon feedstock to a hydro-isomerization reaction under conditions of a temperature of 200° C. to 500° C., a hydrogen pressure of 1 to 200 atmospheres, a liquid space velocity (LHSV) of 1.0 to 10.0 $hr^{-1}$, and a hydrogen/feedstock ratio of 45 to 1780 $Nm^3/m^3$ in the presence of the zeolite catalyst of claim 1.

10. The method of claim 9, wherein at least some of the hydrocarbons in the feedstock have a number of carbon atoms of at least 22.

\* \* \* \* \*